(12) United States Patent
Hohlrieder (10) Patent No.: US 11,207,163 B2
(45) Date of Patent: Dec. 28, 2021

(54) MEDICAL ARRANGEMENT FOR SHUTTING OFF A BODY CHANNEL

(71) Applicant: A.M.I. AGENCY FOR MEDICAL INNOVATIONS GMBH, Feldkrich (AT)

(72) Inventor: Martin Hohlrieder, Gotzis (AT)

(73) Assignee: A.M.I. Agency for Medical Innovations GmbH, Feldkirch (AT)

( * ) Notice: Subject to any disclaimer, the term of this patent is extended or adjusted under 35 U.S.C. 154(b) by 468 days.

(21) Appl. No.: 16/303,379

(22) PCT Filed: Jun. 1, 2017

(86) PCT No.: PCT/AT2017/000046
§ 371 (c)(1),
(2) Date: Nov. 20, 2018

(87) PCT Pub. No.: WO2017/214644
PCT Pub. Date: Dec. 21, 2017

(65) Prior Publication Data
US 2020/0315763 A1   Oct. 8, 2020

(30) Foreign Application Priority Data
Jun. 14, 2016   (AT) .................................. A 293/2016

(51) Int. Cl.
*A61F 2/00*   (2006.01)
(52) U.S. Cl.
CPC ...... *A61F 2/004* (2013.01); *A61F 2250/0009* (2013.01); *A61F 2250/0013* (2013.01)
(58) Field of Classification Search
CPC .......... A61F 2/00; A61F 2/004; A61F 2/0004; A61F 2/0031; A61F 2/0036; A61F 2/0009; A61F 2/0013; A61F 2/0054
See application file for complete search history.

(56) References Cited

U.S. PATENT DOCUMENTS

| 3,863,622 A | 2/1975 | Buuck |
| 4,222,377 A | 9/1980 | Burton |

(Continued)

FOREIGN PATENT DOCUMENTS

| CN | 101460218 | 6/2009 |
| CN | 105393100 | 3/2016 |

(Continued)

OTHER PUBLICATIONS

Artifical Urinary Sphincter, WIKIPEDIA, 2 pages, downloaded on Apr. 19, 2016, https://en.wikipedia.org/wiki/Artificial_urinary_sphincter.

*Primary Examiner* — John P Lacyk
(74) *Attorney, Agent, or Firm* — Volpe Koenig (57) ABSTRACT

A medical device for shutting off a body channel is provided including a band section that can be placed around the body tissue surrounding a body channel and can be closed to form a ring enclosing a passage opening for the body tissue, and has a cavity which makes up one part of a working fluid receiving chamber of the device, for receiving working fluid, and a pump unit for conveying the working fluid. The passage opening is made smaller by introducing the working fluid into the cavity. The arrangement also includes a storage container that has a flexible wall which delimits a storage chamber, wherein to apply an additional force to the body tissue guided through the passage opening, the volume of the storage chamber is made smaller by increasing an ambient pressure acting on the storage container, and the wall of the storage container is at least substantially non-extensible.

12 Claims, 6 Drawing Sheets

(56) References Cited

U.S. PATENT DOCUMENTS

| | | |
|---|---|---|
| 4,417,567 A | 11/1983 | Trick |
| 4,721,509 A | 1/1988 | Craggs |
| 4,784,660 A | 11/1988 | Fischell |
| 5,478,305 A | 12/1995 | Craggs |
| 5,976,109 A | 11/1999 | Heruth |
| 6,461,292 B1 | 10/2002 | Forsell |
| 6,470,892 B1 | 10/2002 | Forsell |
| 6,475,136 B1 | 11/2002 | Forsell |
| 7,172,607 B2 | 2/2007 | Hofle et al. |
| 7,217,237 B2 | 5/2007 | Wassermann et al. |
| 10,139,304 B2 | 11/2018 | Lamraoui |
| 2003/0045775 A1 | 3/2003 | Forsell |
| 2003/0105385 A1 | 6/2003 | Forsell |
| 2004/0260319 A1 | 12/2004 | Egle |
| 2006/0183967 A1 | 8/2006 | Lechner |
| 2006/0211913 A1 | 9/2006 | Dlugos et al. |
| 2007/0156013 A1 | 7/2007 | Birh |
| 2009/0248109 A1 | 10/2009 | Forsell |
| 2010/0076254 A1 | 3/2010 | Jimenez et al. |
| 2010/0211175 A1 | 8/2010 | Gomez-Llorens |
| 2012/0123195 A1 | 5/2012 | Woodruff et al. |
| 2012/0130157 A1 | 5/2012 | Cotner et al. |
| 2012/0157759 A1 | 6/2012 | Wirbisky et al. |
| 2014/0364686 A1 | 12/2014 | McClurg |
| 2015/0359617 A1 | 12/2015 | Forsell |
| 2016/0089224 A1 | 3/2016 | Taylor |
| 2017/0252141 A1 | 9/2017 | Al Harmi et al. |

FOREIGN PATENT DOCUMENTS

| | | |
|---|---|---|
| DE | 9308196 | 12/1993 |
| DE | 10013519 | 10/2001 |
| DE | 202007004083 | 8/2007 |
| EP | 0348114 | 12/1989 |
| EP | 1389453 | 3/2007 |
| EP | 1484038 | 8/2007 |
| EP | 1832253 | 9/2007 |
| EP | 1992315 | 11/2008 |
| EP | 2123238 | 11/2009 |
| EP | 2400239 | 12/2011 |
| FR | 1291158 | 5/1961 |
| FR | 2373272 | 7/1978 |
| WO | 2009136121 | 11/2009 |
| WO | 2009136124 | 11/2009 |
| WO | 2017205883 | 12/2017 |
| WO | 2017214643 | 12/2017 |

MEDICAL ARRANGEMENT FOR SHUTTING OFF A BODY CHANNEL

BACKGROUND

The present invention relates to a medical device for shutting off an anatomical channel, said device comprising a band part which can be placed around the body tissue surrounding the anatomical channel and which can be closed to form a ring that encloses a through-opening for the body tissue, which band part has a hollow chamber constituting a part of a working fluid receiving space of the device for receiving working fluid, and a pump unit which serves to convey the working fluid, wherein the through-opening can be made smaller by introducing the working fluid into the hollow chamber, and a storage container with a flexible wall delimiting a storage chamber, wherein, in order to apply an additional force to the body tissue guided through the through-opening, the volume of the storage chamber can be made smaller by increasing an ambient pressure acting on the storage container.

Medical devices for shutting off an anatomical channel are used, inter alfa, as artificial (sphincter) muscles for aiding or replacing weakened natural muscles in the human or animal body. Examples of the uses of such devices are anal bands for closing an anus, possibly an artificial anus, and artificial sphincter muscles for closing the urethra in order to treat incontinence. Further areas of use are, for example, bands for closing a bile duct. The band part of such medical devices is also designated as a cuff, sleeve or artificial sphincter.

The hollow chamber of the band part can be emptied by the user when necessary in order to increase the cross-sectional area of the through-opening and to allow substances and/or liquids contained in the anatomical channel to pass through. For example, in the use as an artificial sphincter muscle for the urethra, there is often a subsequent automatic closure of the anatomical channel by reverse pumping of working fluid (optionally via a throttle valve) into the hollow chamber of the band part. In an artificial urinary sphincter of this kind for male patients, a pump unit for pumping working fluid is usually implanted in the scrotum. The pumping of working fluid out of the hollow chamber can then be effected by pressure exerted on a flexible part of the pump unit. The reverse pumping of working fluid into the hollow chamber can be effected by a resiliently elastic element of the pump unit. The through-opening of the medical device can often also be made smaller again by deliberate manipulation by the user, i.e. by manual actuation of the pump unit.

A problem with medical devices for narrowing or shutting off an anatomical channel is that they can cause erosion of the body tissue as a consequence of the pressure exerted on the body tissue by the device. Therefore, the pressure of the working fluid in the hollow chamber is generally chosen such that the erosion of body tissue can be kept to a minimum while, at the same time, reliable shutting-off of the anatomical channel is still achieved.

In the event of straining of the abdominal muscles, which occurs, in most cases involuntarily, for example when climbing stairs, lifting loads, sneezing, coughing or laughing, there is a brief increase in intra-abdominal pressure. The short-lived pressure peaks act in particular on the internal (hollow) organs arranged in the abdominal space, e.g. the bladder and intestines. The pressure in the (hollow) organs thus increases, which can lead to substances and/or liquid escaping through the portion of the anatomical channel shut off by the band part. This type of incontinence is also referred to as stress incontinence.

U.S. Pat. No. 5,478,305 A discloses a medical device which is of the type mentioned at the outset and which is used for treating urinary or fecal incontinence. The band part, referred to as a cuff in said document, is made of silicone. By filling the cuff with working fluid, the pressure in the hollow space of the cuff rises, and the resulting displacement of the inner portion of the cuff in the direction toward the longitudinal center axis closes the anatomical channel. A storage container in the form of a flexible balloon (stress balloon) made of elastically extensible silicone is arranged between two portions of a working fluid line which brings a pump into fluidic communication with the cuff. The storage chamber formed by the stress balloon is filled with working fluid. A brief increase of the internal body pressure causes a decrease in volume of the storage chamber of the stress balloon, as a result of which working fluid is forced into the cuff. By means of the brief increase in the pressure of the working fluid, the anatomical channel can also be kept shut off during a stress event, and leakage can be prevented. When the internal body pressure decreases again, the volume of the storage chamber of the stress balloon increases and the pressure of the working fluid decreases, wherein working fluid flows out of the cuff. When the pressure of the working fluid in the cuff is increased in order to close the anatomical channel, the volume of the stress balloon also increases, such that a correspondingly large quantity of liquid has to be displaced by the pump.

SUMMARY

The object of the invention is to make available an advantageous device which is of the type mentioned at the outset and which can be used to treat stress incontinence.

This is achieved by a device having one or more features of the invention.

In the medical device according to the invention, provision is made that the wall of the storage container is designed to be at least substantially non-extensible.

As the storage container fills, there is at least substantially no extension of the material of the wall, i.e. the volume of the storage chamber can be increased substantially only by unfolding of the flexible wall. The volume of the storage chamber is therefore limited to a maximum storage volume of the storage chamber.

A configuration of a wall as flexible signifies that said wall is able to bend, in particular able to fold up.

The storage container is implantable in the body, in particular in the abdominal space, wherein the internal pressure in the body acts on the storage container. When the abdominal muscles strain during a stress event, the volume of the storage chamber of the storage container changes as a result of an increase in the ambient pressure (=internal body pressure). During a stress event, the ambient pressure acting the storage container is at any rate above the atmospheric pressure.

"Substantially non-extensible" signifies the material property of the wall of the storage container whereby, starting from a state of maximum deployment, the volume of the storage chamber remain substantially unchanged when the pressure in the storage chamber increases during the operation of the device. The customary pressures acting within the body during the operation of the medical device are decisive in this regard. Provision is preferably made that, starting from a state of maximum deployment, the volume of the storage chamber increases by less than 10%, preferably by less than 5%, when the pressure in the storage chamber increases by 0.1 bar.

The wall of the storage container can have an at least substantially non-extensible reinforcement. The reinforcement can be configured like a net, for example. The reinforcement expediently has an elastic modulus of at least 1,000 N/mm$^2$, preferably of at least 5,000 N/mm$^2$. The wall can, for example, have a matrix of silicone in which the reinforcement is embedded.

As an alternative or an addition to an at least substantially non-extensible reinforcement of this kind, the wall of the storage container can have or be composed of a layer of an at least substantially non-extensible plastic film. For example, the plastic film could be produced from polyethylene, polyamide or the like. The elastic modulus of the plastic film is preferably at least 1,000 N/mm$^2$, particularly preferably at least 5,000 N/mm$^2$. In particular, when using a wall comprised of a plastic film, provision can be made that the wall is pliable. That is to say, the wall does not return to an earlier shape spontaneously (=without the action of an external force). The pliable wall could also be referred to as dimensionally unstable.

In a first possible embodiment of the invention, provision is made that the storage chamber constitutes a part of the working fluid receiving space, wherein the pressure of the working fluid can be increased by reducing the volume of the storage chamber in order to apply the additional force. When the pressure acting on the storage chamber from the outside, i.e. the ambient pressure (=internal body pressure), increases to a sufficiently high level (above the pressure of the working fluid) in a stress event, the pressure of the working fluid is increased by the reduction of the volume of the storage chamber. The pressure (=pressure of the working fluid) in the hollow chamber of the band part thus also increases accordingly, as a result of which an additional force can be exerted on the body tissue. As the internal body pressure, and therefore the pressure of the working fluid, decreases again, the volume of the storage chamber of the storage container increases as working fluid is admitted, in particular as far as the maximum storage volume of the storage chamber.

In this embodiment, the storage container can be arranged, for example, between two portions of the working fluid line that connects the hollow chamber of the band part to the pump unit. Provision can also be made, however, that the storage container is connected to the pump unit via a separate connection line.

In a second possible embodiment of the invention, provision is made that the storage chamber forms part of an auxiliary fluid receiving space of the device for receiving an auxiliary fluid separate from the working fluid, and the auxiliary fluid receiving space moreover comprises an expansion chamber of an expansion body of the device.

The auxiliary fluid is completely separate from the working fluid, i.e. no fluid exchange takes place between the auxiliary fluid and the working fluid.

When a stress event occurs, e.g. caused by an increase of the internal body pressure during a fit of coughing, the expansion chamber of the expansion body increases in size as a result of a reduction of the volume of the storage chamber caused by a sufficiently high pressure acting on the storage container from the outside. The increase in the volume of the expansion chamber by admission of auxiliary fluid into the expansion chamber is effected in particular by stretching or unfolding of the expansion body. For this purpose, provision can be made that the expansion body is elastically extensible. However, in other embodiments, the expansion body can also be formed from an at least substantially non-extensible material.

In a first possible variant of this second embodiment of the invention, provision is made that the expansion body is arranged in the working fluid receiving space. As the expansion chamber fills with auxiliary fluid, with the volume of the expansion chamber increasing as a result, the pressure of the working fluid increases, wherein the inner portion of the band part is displaced farther in the direction of the longitudinal center axis of the through-opening. This leads to greater compression of the body tissue surrounding the anatomical channel. The expansion body could be arranged, for example, in the hollow chamber of the band part or of the working fluid line. The expansion body is particularly preferably arranged in the pump unit.

In a second possible variant of this second embodiment of the invention, the expansion body is arranged at the band part, on a side of the band part directed toward the through-opening, i.e. on the inner portion of the band part. The filling of the expansion chamber with auxiliary fluid causes an increase in the volume of the expansion chamber, which acts with a compressing effect directly on the body tissue surrounding the anatomical channel. In this way, it is possible to ensure that the anatomical channel is reliably shut off during a stress event.

BRIEF DESCRIPTION OF THE DRAWINGS

Further advantages and details of the invention are explained below with reference to the attached drawings, in which.

DETAILED DESCRIPTION

A band part 1 of the medical device can be placed in a ring shape around the body tissue 2 surrounding the anatomical channel, here the urethra. The band part 1 has a hollow chamber 3 which extends in the direction of the longitudinal extent of the band part 1, in the illustrative embodiments substantially along the entire length of the band part 1. The band part 1 is thus configured like a hose, with ends closed at both sides.

Figure 6:
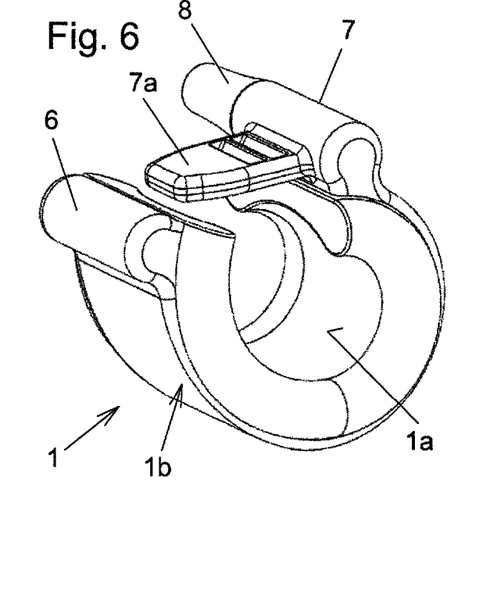
FIGS. 6 and 7 show perspective views of the free, i.e. not implanted, band part of the device in an opened state and a closed state, specifically corresponding to the release state.

A first and a second closure part 6, 7 are arranged at the two ends of the band part 1. The first closure part 6 has an insertion opening 6*a* into which a tongue 7*a* of the second closure part 7 can be inserted and locked therein (cf. FIG. 6).

Figure 7:
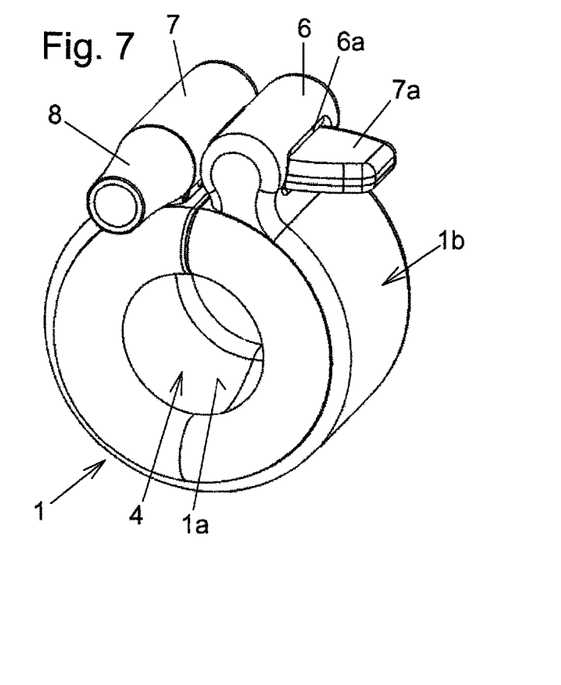

The closure parts 6, 7 thus form a closure with which the band part 1 can be closed to form a ring, in particular a circular ring (cf. FIG. 7). In the closed state, the band part 1 encloses a through-opening 4 for the body tissue 2 surrounding the anatomical channel.

A working fluid, in particular a liquid, e.g. saline solution, is located in the hollow chamber 3. The size of the through-opening 4 depends on the quantity of the working fluid in the hollow chamber 3. The through-opening 4 can be made smaller by introducing working fluid into the hollow chamber 3. A flexible inner portion 1*a* of the band part 1, which portion is adjacent to the longitudinal center axis 5 of the through-opening 4, is displaced in the direction toward the longitudinal center axis 5, as is known. By removing working fluid from the hollow chamber 3, the through-opening 4 can be made larger again.

Figure 8:
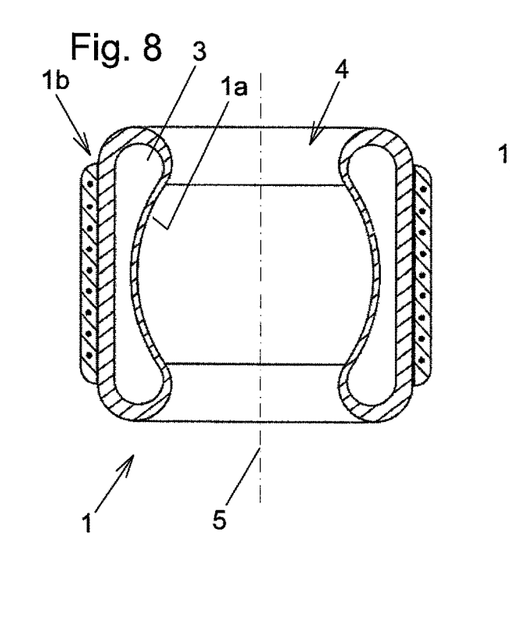
FIG. 8 shows a longitudinal center section (parallel to the longitudinal center axis of the through-opening and extending through the latter) through the band part in the state according to FIG. 7.
Figure 9:
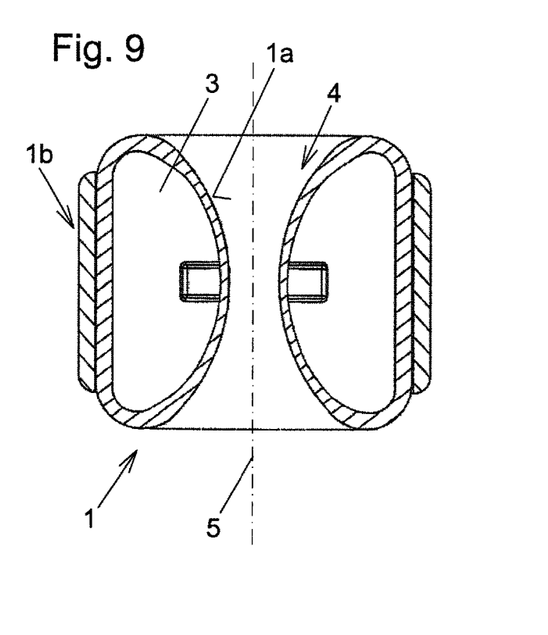
FIG. 9 shows a longitudinal center section analogous to FIG. 8, but in the shut-off state of the band part.

FIG. 8 shows the state in which the through-opening 4 is at its largest (wherein the pressure of the working fluid in the hollow chamber 3 corresponds to the ambient pressure). FIG. 9 shows a state in which it is filled with the working fluid, in particular the state in which it is filled to the maximum with working fluid (wherein the pressure of the working fluid in the hollow chamber 3 is above the ambient pressure). The formation of folds, which would occur in particular if the band part is not placed around the ureter, is not shown in FIG. 9. By contrast, a rear portion 1*b* of the band part 1, set back from the longitudinal center axis 5, can be made stiff in relation to the inner portion 1*a*, in particular by a reinforcing layer, as a result of which a deformation of the rear portion 1*b* can be at least largely avoided.

Figure 1:
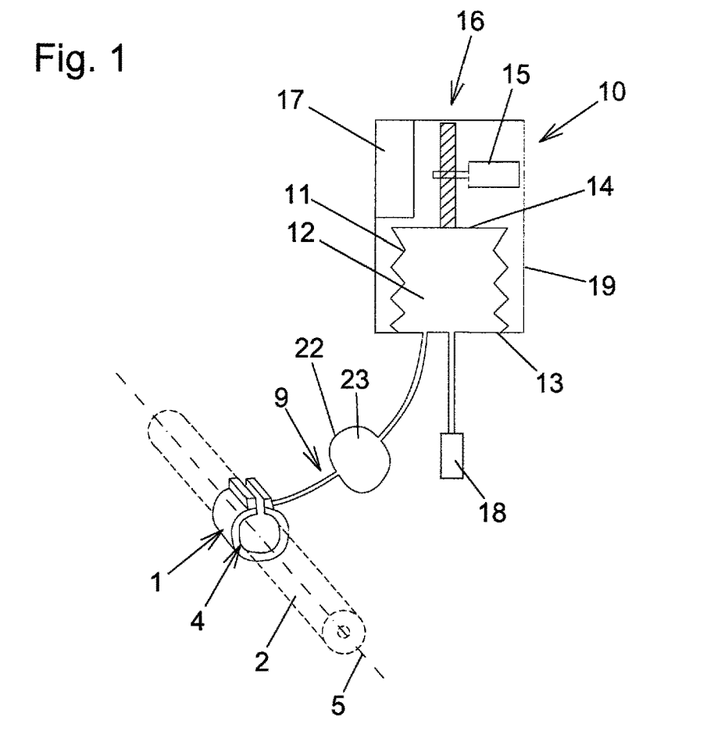
FIG. 1 shows a schematic view of a first illustrative embodiment of a medical device configured as an artificial urethral sphincter, in a release state of the band part, in which state the ureter is opened.
Figure 2:
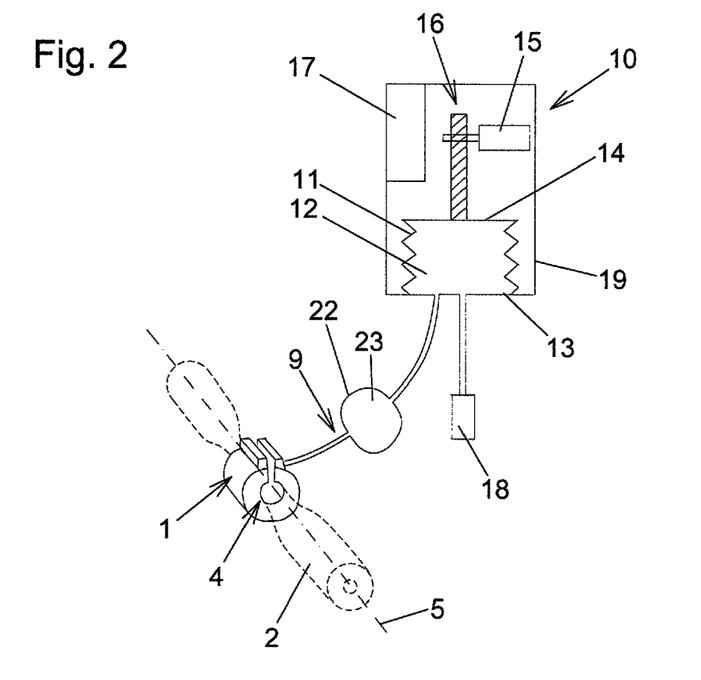
FIG. 2 shows a view analogous to FIG. 1, in a shut-off state of the band part, in which state the ureter is closed.

In the closed state of the band part 1 placed around the anatomical channel, said band part 1 can thus adopt a release state, in which the anatomical channel is opened (cf. FIG. 1), and a shut-off state, in which the anatomical channel is closed (cf. FIG. 2). In the release state, the pressure of the working fluid in the hollow chamber 3 can for example correspond to the atmospheric pressure. In the shut-off state, the hollow chamber 3 is filled with such a quantity of working fluid that the anatomical channel is closed.

Various modifications of the design of the band part are conceivable and possible. For example, it would be possible for special closure parts mounted on the band part 1 to be omitted altogether and for the two ends of the band part to be sewn to each other.

The band part 1 can be made from silicone in a known manner. Other biocompatible materials may also be used in principle.

In the illustrative embodiment, an attachment stub 8 is integrally formed on one of the closure parts, the interior of which attachment stub 8 is connected to the hollow chamber 3 via a channel running through the closure part 7. Such an attachment stub could also be provided at another location of the band part. A working fluid line 9 configured as a hose is attached at the attachment stub 8.

The channel, running through the closure part 7, and the hollow chamber 3 each form a part of a working fluid receiving space for receiving working fluid. The working fluid receiving space of the medical device comprises the entirety of the continuous interior of the device in which working fluid is located during operation. Moreover, the inner channel of the working fluid line 9 and an interior 12 of a pump part 11, filled with working fluid during the operation of the device, each form a part of the working fluid receiving space for the working fluid. The band part 1 is connected by the working fluid line 9 to the pump part 11 of the pump unit 10, which is spatially separate from the band part 1 (cf. FIGS. 1 to 3). By use of the pump unit 10, the quantity of working fluid in the hollow chamber 3 of the band part 1 can be changed.

In the illustrative embodiments, the pump part 11 is formed by a bellows which is closed by a bottom part 13 and a cover part, the latter constituting an actuating element 14. An electric drive 15 acts on the actuating element 14 via a gear 16, for example a worm gear, in order to change the volume of the interior 12. The gear 16 is expediently self-locking, such that an adopted position of the actuating element 14 is maintained without supply of electrical energy to the drive 15.

In the illustrative embodiment, the pump part 11 thus forms at the same time a reservoir for the working fluid with which the hollow chamber 3 of the band part 1 is filled in order to close the anatomical channel. For example, the pump part 11 could also be formed by a piston-cylinder unit, in which case the actuating element 14 would be formed by the piston of this piston-cylinder unit.

The electric drive 15 is controlled by a control electronics unit 17 of the pump unit 10, which also has a battery (not shown) for supplying electric current to the drive 15. The control electronics unit 17 is operated by the user via a suitable user interface (not shown). The user interface can be an operating unit that is linked to the control electronics unit 17 by wire or by radio and that has corresponding switches.

The user interface can be arranged outside the body. Implantation of the user interface is conceivable and possible. A separate user interface could in principle also be omitted, in which case at least one operating element activatable by the user would be arranged at the pump unit 10. This would accordingly have to be able to be activated from outside the body.

The components of the pump unit 10 are arranged in a housing 19. The housing 19 is made of a biocompatible material or is encased by such a material.

To fill the working fluid receiving space of the medical device with working fluid, a port 18 is provided in the customary way. This port 18 can be attached to the pump part 11 via a hose, for example.

The medical device moreover has a storage container 22 with a storage chamber 23.

In the first illustrative embodiment, the storage container 22 is arranged between two portions 9', 9" of the working fluid line 9 which connects the hollow chamber 3 of the band part 1 to the interior 12 of the pump part 11. During the operation of the device, the storage chamber 23 is filled with working fluid and thus forms a part of the working fluid receiving space of the device.

The storage chamber 23 of the storage container 22 is delimited by a flexible wall 22*a*. The latter is designed to be at least substantially non-extensible. That is to say, during the operation of the device, starting from a state of maximum deployment of the storage container 22, the volume of the storage chamber 23 does not substantially increase when the pressure in the storage chamber 23 rises. In the first illustrative embodiment, the pressure in the storage chamber 23 corresponds to the pressure of the working fluid.

In the illustrative embodiment, an increase of the pressure in the storage chamber 23 (=pressure of the working fluid) of the maximally deployed storage container 22 by 0.1 bar (starting from the pressure present in the shut-off state of the band part 1) leads at most to an increase of the volume of the storage chamber 23 of less than 5%.

The wall 22a of the storage container 22 has an at least substantially non-extensible reinforcement 22b. The reinforcement 22b expediently has an elastic modulus of at least 1,000 N/mm$^2$, preferably of at least 5,000 N/mm$^2$. The reinforcement 22b is embedded in a base material (=matrix) of the wall 22a (cf. FIGS. 4 and 5). In the illustrative embodiment, the base material is composed of silicone.

The reinforcement 22b is configured like a net, i.e. individual fibers or strands of the reinforcement are joined at points of intersection form rectangular or diamond-shaped meshes of the reinforcement 22b. The net-like reinforcement 22b could also be designated as a braiding.

Figures 3, 4:
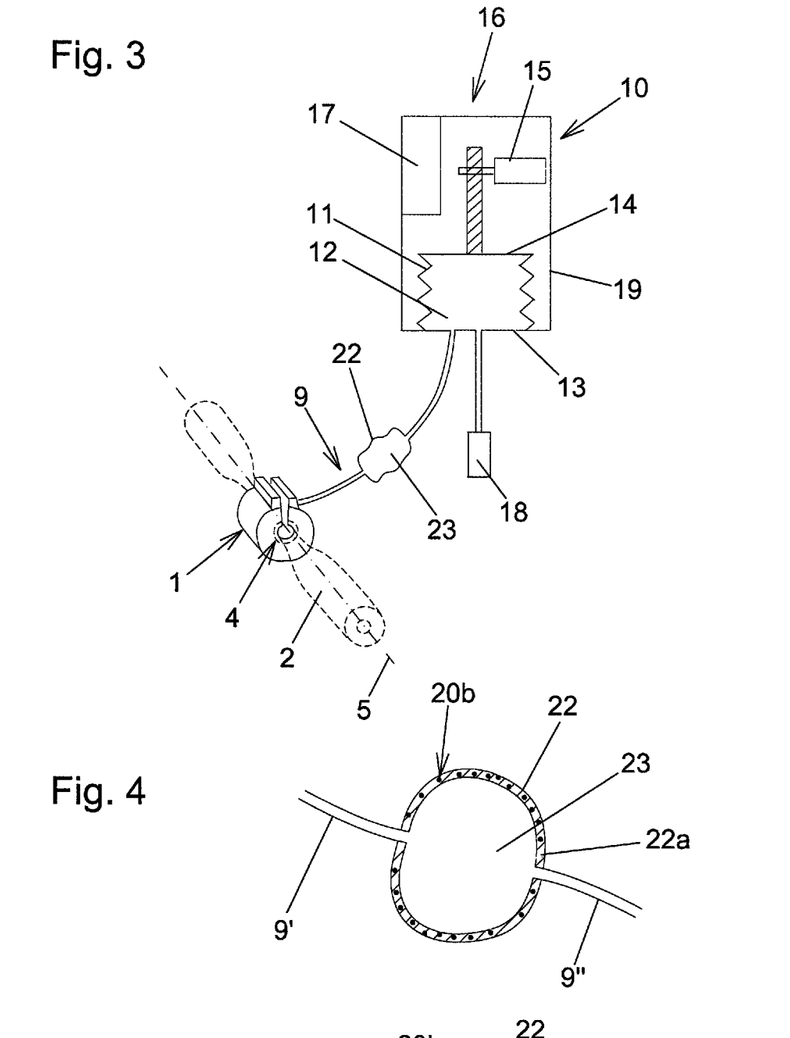
FIG. 3 shows a view analogous to FIG. 1, in a stress state of the band part, in which state an additional force is exerted on the ureter.
FIGS. 4 and 5 show sectional views of the storage container corresponding to FIGS. 2 and 3.
Figure 5:
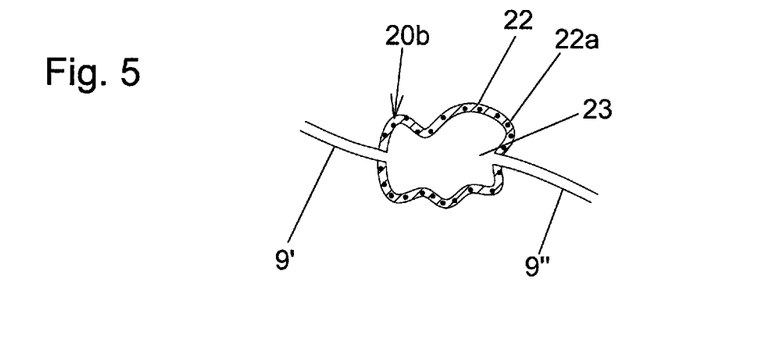

The storage container 22 can fold up, wherein the volume of the storage chamber 23 can be changed through a folding up or unfolding of the storage container 22 (cf. FIGS. 4 and 5). Folding-up can in particular take place through an increase of the ambient pressure (=internal body pressure) to a pressure above the pressure of the working fluid.

As an alternative or addition to the reinforcement 22b, the wall 22a of the storage container 22 could have an at least substantially non-extensible plastic film or could be formed by an at least substantially non-extensible plastic film. In a design of the wall 22a from a plastic film 22a, provision could be made that the wall is designed to be pliable, i.e. the wall 22a does not then return spontaneously to an earlier shape. The pliable wall 22a could also be referred to as dimensionally unstable.

The plastic film expediently has an elastic modulus of at least 1,000 N/mm$^2$, preferably of at least 5,000 N/mm$^2$.

The plastic film could be of polyethylene or polyamide, for example.

In the release state of the band part 1 as shown in FIG. 1 and in the shut-off state of the band part 1 as shown in FIG. 2, the volume of the storage chamber 23 corresponds to a maximum value of the volume (=storage volume). Thus, the volume of the storage chamber 23 does not change here between the release state and the shut-off state of the band part 1 (provided that an additional pressure does not act on the storage container 22 from the outside; see the description farther below). However, provision could also be made that the volume of the storage chamber 23 in the release state of the band part 1 is smaller than the maximum storage volume of the storage chamber 23, i.e. the storage container 22 is then not completely deployed.

If the pressure within the body (=internal body pressure) increases, e.g. because of a coughing fit, a force brought about by the internal body pressure acts directly on the storage container 22. If the internal body pressure is greater than the pressure of the working fluid in the shut-off state of the band part 1, then the storage container 22 is compressed. The pressure of the working fluid increases as a result, wherein working fluid is additionally introduced into the hollow chamber 3 of the band part 1. The inner portion 1a of the band part 1 is displaced in the direction toward the longitudinal center axis, and in this process an additional force is applied to the body tissue 2 guided through the through-opening 4. This state of the band part 1 is referred to in this document as the stress state of the band part 1 and is shown in FIG. 3.

As the internal body pressure, and therefore the pressure of the working fluid, subsequently decreases, the volume of the storage chamber 23 of the storage container 22 increases as it receives working fluid. After the stress event, the band part 1 is thus located again in the shut-off state (cf. FIG. 2).

Since the wall 22a of the storage container 22 is designed to be at least substantially non-extensible, this means that the storage container 22, during the filling of the storage chamber 23 and the increase of volume (starting from a folded-up state of the storage container 22), exerts substantially no elastic restoring force on the content of the storage chamber, which content, in the first illustrative embodiment, is working fluid. When the anatomical channel is to be opened from the shut-off state of the band part 1, e.g. to pass urine, i.e. when the band part 1 adopts the release state (see FIG. 1 for example) by displacement of working fluid from the hollow chamber 3 into the interior 12 of the pump part 11, and when there is also no stress event, the change of volume of the storage chamber 23 remains substantially equal to zero or relatively slight. Therefore, during the adjustment of the band part 1 from the shut-off state to the release state, and vice versa, no working fluid or only a little working fluid has to be conveyed out of and into the storage container 22. The quantity of working fluid to be displaced can thus be minimized, and the associated energy consumption for displacement of working fluid can be reduced. The interval for charging or replacing the battery of the control electronics unit 17 can thus be lengthened.

Figure 10:
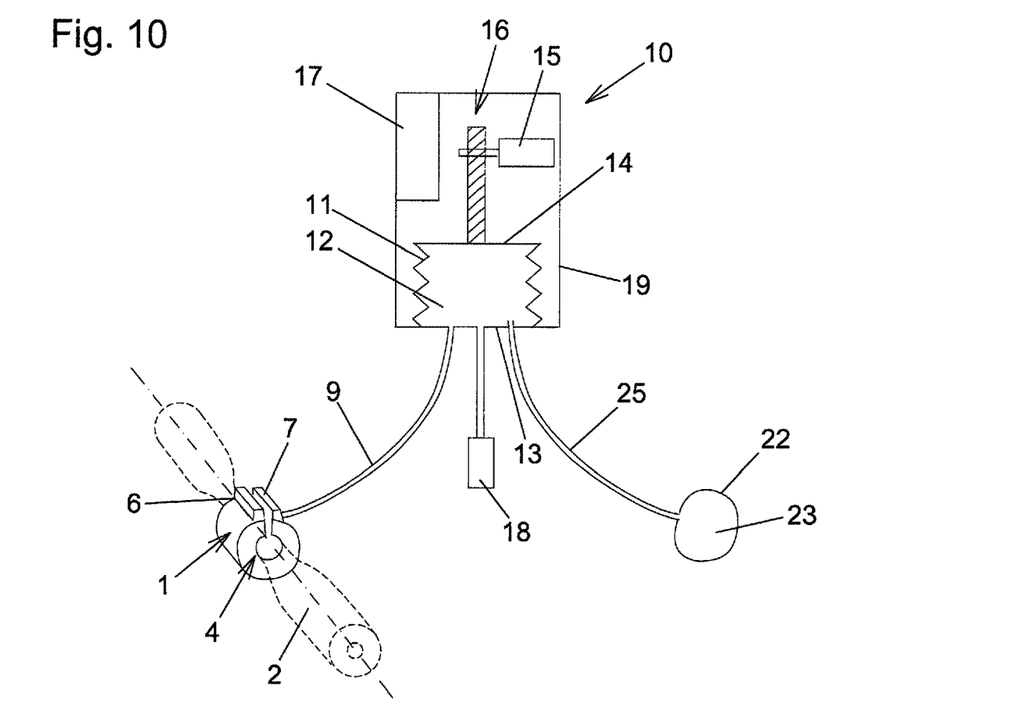
FIG. 10 shows a schematic view of a second embodiment of an artificial urethral sphincter according to the invention, in a shut-off state of the band part, in which state the ureter is closed.
Figure 11:
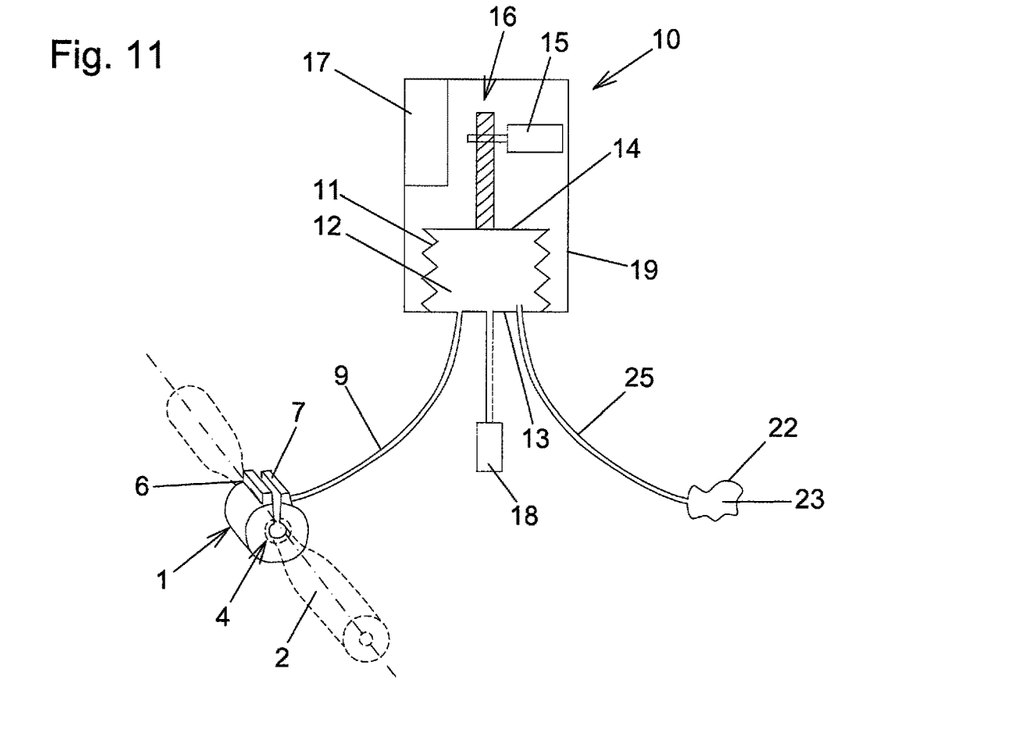
FIG. 11 shows a view analogous to FIG. 10 in a stress state of the band part, in which state an additional force is exerted on the ureter.

FIGS. 10 and 11 show a second illustrative embodiment of a medical device according to the invention. The structure of the pump unit 10 and of the band part 1 corresponds to that of the first illustrative embodiment, and therefore the explanations concerning the second illustrative embodiment focus mainly on the differences in relation to the first illustrative embodiment. Apart from the differences set out below, the explanations concerning the first illustrative embodiment also apply to the second illustrative embodiment. Thus, in terms of the configuration of the wall 22a of the storage container 22 and in terms of the closure parts 6, 7 of the band part 1 that are shown only schematically in FIGS. 10 and 11, reference is made to the explanations concerning the first illustrative embodiment.

In the medical device according to the second illustrative embodiment, provision is made that the storage container 22 is connected to the pump unit 10 via a separate connection line 25. In the second illustrative embodiment too, the storage chamber 23 of the storage container 22 forms a part of the working fluid receiving space of the device. In contrast to the first illustrative embodiment, the storage container 22 has only one attachment for working fluid and is otherwise closed, preferably completely. During a stress event, working fluid is therefore displaced from the storage chamber 23 via the inner channel of the connection line 25 into the interior 12 of the pump part 11. The connection line 25 is configured as a hose.

In other respects, the medical device according to the second illustrative embodiment behaves analogously to the device according to the first illustrative embodiment of the medical device when a stress event occurs, which is why reference is made to the relevant explanations concerning the first illustrative embodiment.

Figure 12:
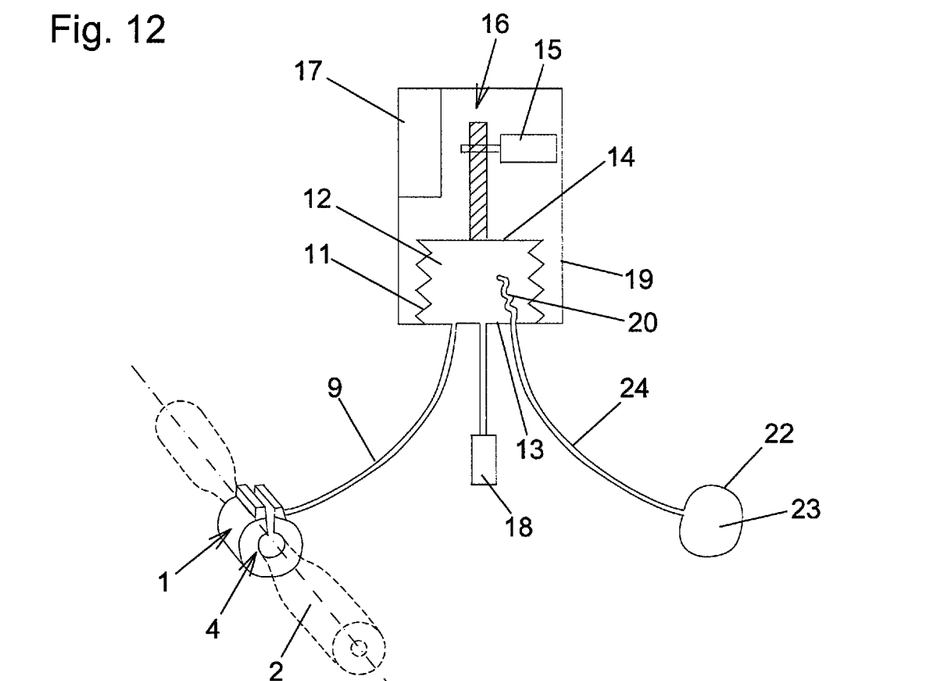
FIG. 12 and FIG. 13 show schematic views of a third illustrative embodiment according to the invention, analogous to FIGS. 10 and 11, and FIGS. 14 and 15 show schematic views of a fourth illustrative embodiment according to the invention, in a shut-off state and a stress state of the band part.
Figure 13:
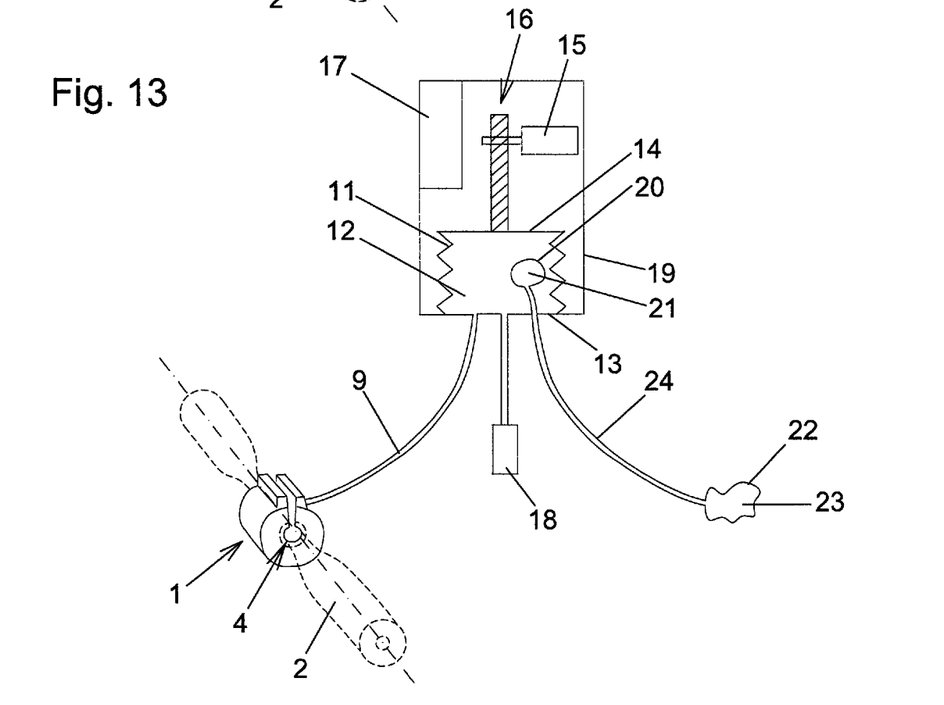

FIGS. 12 and 13 show a third illustrative embodiment of a medical device according to the invention. The structure of the pump unit 10 and of the band part 1 corresponds to that of the first and second illustrative embodiment. The structure of the storage container 22 corresponds to that of the second illustrative embodiment, and therefore the explanations concerning the third illustrative embodiment focus mainly on the differences in relation to the first illustrative embodiment and second illustrative embodiment. Apart from the differences set out below, the explanations concerning the first illustrative embodiment and second illustrative embodiment also apply to the third illustrative embodiment.

In the medical device according to the third illustrative embodiment, provision is made that the storage chamber 23 of the auxiliary fluid container 22 is fluidically connected by an auxiliary fluid line 24 to an expansion chamber 21 of an expansion body 20. The auxiliary fluid, separate from the working fluid, could be introduced into the auxiliary fluid line 24 via a port (not shown in detail) or directly into the storage chamber 23. The auxiliary fluid is expediently a liquid, e.g. saline solution.

In this illustrative embodiment, the storage chamber 23 thus forms a part of an auxiliary fluid receiving space of the device for receiving an auxiliary fluid separate from the working fluid. The expansion chamber and the inner channel of the auxiliary fluid line 24 also form a part of the auxiliary fluid receiving space of the device.

In the third illustrative embodiment, the expansion body 20 is arranged in the working fluid receiving space of the device filled with working fluid, namely in the interior 12 of the pump part 11 (cf. FIGS. 12 and 13). That is to say, the expansion body 20 is surrounded by working fluid.

The volume of the expansion chamber 21 can be increased by introduction of auxiliary fluid into the expansion chamber 21 by unfolding or stretching of the expansion body 20. If the increase in volume is effected purely by unfolding, the expansion body 20 can be made of a non-extensible material, such that the maximum volume of the expansion chamber 21 is limited. Therefore, an increase in the pressure of the working fluid is limited by the limitation of the volume of the expansion chamber 21. However, the volume of the expansion chamber 21 can be increased by an elastically extensible design of the expansion body 20.

The expansion body 20 can also be designed to be pliable, such that the expansion body 21 is then dimensionally unstable, as is indicated in FIG. 12.

At least in the shut-off state of the band part 1 shown in FIG. 12, the auxiliary fluid is at a lower pressure than the working fluid. The expansion chamber 21 of the expansion body is preferably folded up completely. Therefore, there is at least substantially no auxiliary fluid present in the expansion chamber 21. The volume of the expansion chamber 21 is therefore at least substantially equal to zero. In a modified embodiment, this could in principle also be otherwise.

Moreover, in the release state (not shown) of the band part 1, the expansion chamber 21 could be folded up completely, i.e. with a volume substantially equal to zero. This is the case if the auxiliary fluid is at a lower pressure than the working fluid and/or if the auxiliary fluid is forced out of the expansion chamber 21 by the elasticity of the expansion body 20 when there is equality of the pressure (of the auxiliary fluid and of the working fluid). A certain residual volume of the expansion chamber 21 may also be present in the release state.

If the pressure within the body (=internal body pressure) now rises, for example during a coughing fit, the force brought about by the internal body pressure acts directly on the storage container 22. When a force acts on the storage container 22, the pressure of the auxiliary fluid increases correspondingly. If the internal body pressure, and therefore the pressure of the auxiliary fluid, is greater than the pressure of the working fluid, the storage container 22 is compressed and auxiliary fluid is forced out of the storage chamber 23 into the expansion chamber 21. If the expansion body 20 sets an elastic restoring force counter to the expansion of the expansion chamber 21, this elastic restoring force can also be overcome by the pressure of the auxiliary fluid (the expansion body 20 is thus expanded only when the ambient pressure exceeds the pressure of the working fluid to such an extent that the elastic restoring force is also overcome by the pressure of the auxiliary fluid). The resulting increase of the volume of the expansion chamber 21 leads to an increase of the pressure in the interior 12 of the pump part 11. Working fluid is ejected from the interior 12 and introduced into the hollow chamber 3 of the band part. The inner portion 1a of the band part 1 is thus displaced in the direction toward the longitudinal center axis 5, and the additional force is applied to the body tissue 2 guided through the through-opening 4. This state of the band part 1 (=stress state) is shown in FIG. 13.

As the internal body pressure, and therefore the pressure of the auxiliary fluid, subsequently decreases again such that the pressure of the auxiliary fluid is less than the pressure of the working fluid (if appropriate plus the elastic restoring force of the expansion body 20), the volume of the storage chamber 23 of the storage container 22 increases as it receives auxiliary fluid discharged from the expansion chamber 21 of the expansion body 20. After the stress event, the band part 1 is once again located in the shut-off state (cf. FIG. 12).

Figures 14, 15:
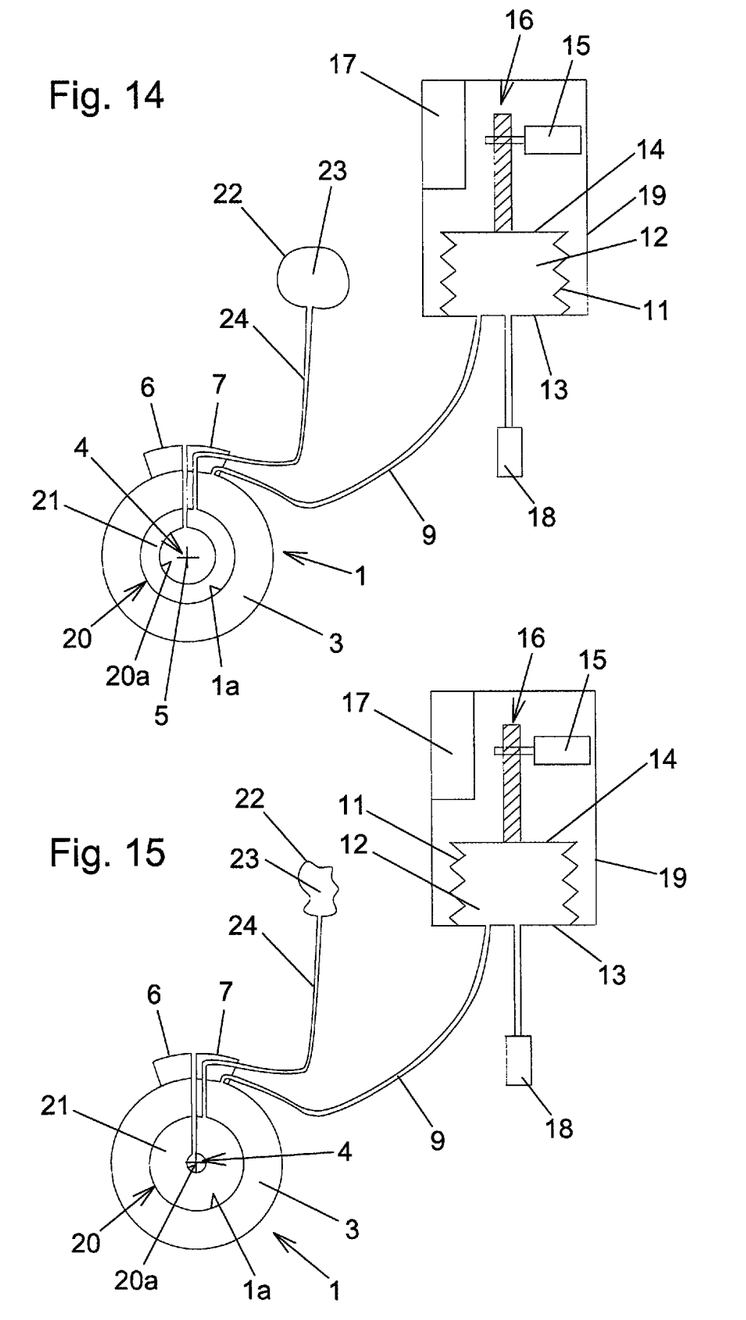

FIGS. 14 and 15 show a fourth illustrative embodiment of a medical device according to the invention. The structure of the pump unit 10 and of the storage container 22 corresponds to that of the preceding illustrative embodiments. The explanations concerning the fourth illustrative embodiment focus mainly on the differences in relation to the third illustrative embodiment. Apart from the differences set out below, the explanations concerning the third illustrative embodiment also apply to the fourth illustrative embodiment.

In the medical device according to the fourth illustrative embodiment, provision is made that the expansion body 20 is arranged at the band part 1, on a side of the band part 1 directed toward the through-opening 4, i.e. on the inner portion 1a. This is shown schematically in FIGS. 14 and 15, wherein the expansion chamber 21 extends in the longitudinal direction of the band part 1, substantially along the entire length of the band part 1. Therefore, in the fourth illustrative embodiment, the expansion body 20 is configured as a hose closed at both ends.

In the closed state of the band part 1, the expansion body 20 arranged at the band part 1 has, in relation to the circumferential direction of the longitudinal center axis 5, a substantially encircling bearing surface 20a for bearing on the body tissue 2.

In the shut-off state of the closed band part 1, the hollow chamber 3 is filled with such a quantity of working fluid that the anatomical channel is closed (cf. FIG. 14). The pressure of the working fluid corresponds to the counter-pressure exerted by the body tissue plus any elastic restoring force of the band part 1 that has to be overcome.

When working fluid is drained off, the band part 1 adopts the release state (not shown) in which the anatomical channel is opened.

If, starting from the shut-off state of the band part 1 shown in FIG. 14, the pressure within the body (=internal body pressure) increases in the presence of a stress event, this internal body pressure acts on the storage container 22. If the internal body pressure, and therefore the pressure of the auxiliary fluid, is greater than the counter-pressure applied by the body tissue to the expansion body 20, the storage container 22 is compressed and auxiliary fluid is forced out of the storage chamber 23 into the expansion chamber 21 of the expansion body 20. If the expansion body 20 sets an elastic restoring force counter to the expansion of the expansion chamber 21, this elastic restoring force is also overcome by the pressure of the auxiliary fluid. As a result of the increase in the volume of the expansion chamber 21, the expansion body 20 acts with a compressing effect directly on the body tissue 2 surrounding the anatomical channel, in order to ensure reliable shutting-off of the anatomical channel during a stress event (cf. the stress state of the band part 1 shown in FIG. 15, in which state an additional force is applied to the body tissue 2 guided through the through-opening 4). The body tissue 2 itself is not indicated in FIGS. 14 and 15.

When the internal body pressure again reaches a basic state, i.e. without a stress event being present, the auxiliary fluid flows back out of the expansion chamber 21 into the auxiliary fluid container 22 (cf. the shut-off state of the band part 1 shown in FIG. 14).

The reverse flow of the auxiliary fluid into the storage container 22 is thus effected by the counter-pressure exerted by the body tissue 2, together with the pressure exerted on the expansion body 20 by the hollow chamber 3 filled with working fluid. If the expansion body 20 sets an elastic restoring force counter to the expansion of the expansion chamber 21, this elastic restoring force can have a supporting effect in the reverse flow of the auxiliary fluid.

In the fourth illustrative embodiment, provision can be made that the expansion body 20 and the band part 1 are formed materially in one piece. Provision is advantageously made that the expansion body 20 is designed to be elastically extensible. In another embodiment, however, provision could also be made that the expansion body 20 is designed to be substantially non-extensible and/or pliable.

Besides the pump unit shown in the illustrative embodiments, the storage container could in principle also be used in combination with a pump unit that is commonly known from the prior art and that can be actuated manually, for example.

KEY TO THE REFERENCE NUMBERS

1 band part
1*a* inner portion
1*b* rear portion
2 body tissue
3 hollow chamber
4 through-opening
5 longitudinal center axis
6 first closure part
6*a* insertion opening
7 second closure part
7*a* tongue
8 attachment stub
9 working fluid line
9', 9" portion of the working fluid line
10 pump unit
11 pump part
12 interior
13 bottom part
14 actuating element
15 drive
16 gear
17 control electronics unit
18 port
19 housing
20 expansion body
20*a* bearing surface
21 expansion chamber
22 storage container
22*a* wall
22*b* reinforcement
23 storage chamber
24 auxiliary fluid line
25 connection line

The invention claimed is:

1. A medical device for shutting off an anatomical channel, comprising
 a band part configured for placement around body tissue surrounding the anatomical channel and that is adapted to be closed to form a ring that encloses a through-opening for the body tissue, the band part including a hollow chamber constituting a part of a working fluid receiving space that is configured to receive working fluid,
 a pump unit configured to convey the working fluid into the hollow chamber, such that the through-opening is made smaller by introduction of the working fluid into the hollow chamber,
 a storage container with a flexible wall delimiting a storage chamber, a volume of the storage chamber is reducible by increasing an ambient pressure acting on the storage container in order to apply an additional force to the body tissue that is guided through the through opening,
 the wall of the storage container is configured to be non-extensible in that, starting from a state of maximum deployment of the storage container, the volume of the storage chamber increases by less than 10% for a 0.1 bar increase in pressure in the storage chamber.

2. The medical device as claimed in claim 1, wherein the storage chamber forms part of an auxiliary fluid receiving space that is adapted to receive an auxiliary fluid separate from the working fluid, and the auxiliary fluid receiving space further comprises an expansion chamber of an expansion body, and the expansion chamber is adapted to be filled with the auxiliary fluid in order to apply the additional force.

3. The medical device as claimed in claim 2, wherein the expansion body is arranged in the working fluid receiving space.

4. The medical device as claimed in claim 2, wherein the expansion body is arranged at the band part, on a side of the band part directed toward the through-opening.

5. The medical device as claimed in claim 1, wherein the storage chamber is part of the working fluid receiving space, and the pressure of the working fluid is increased by reducing the volume of the storage chamber in order to apply the additional force.

6. The medical device as claimed in claim 5, wherein the hollow chamber of the band part is connected to the pump unit by a working fluid line, and the storage container is arranged between two portions of the working fluid line.

7. The medical device as claimed in claim 5, wherein the hollow chamber of the band part is connected to the pump unit by a working fluid line, and the storage container is connected to the pump unit via a separate connection line.

8. The medical device as claimed in claim 1, wherein starting from the state of maximum deployment of the storage container, the volume of the storage chamber increases by less than 5% for a 0.1 bar increase in pressure in the storage chamber.

9. The medical device as claimed in claim 1, wherein the wall of the storage container has a an at least substantially non-extensible reinforcement.

10. The medical device as claimed in claim 1, wherein the wall of the storage container comprises a layer of a non-extensible plastic film.

11. The medical device as claimed in claim 10, wherein an elastic modulus of the plastic film is at least 1.0 N/mm$^2$.

12. The medical device as claimed in claim 9, wherein the non-extensible reinforcement has an elastic modulus of at least 1.0 N/mm$^2$.

* * * * *

UNITED STATES PATENT AND TRADEMARK OFFICE
CERTIFICATE OF CORRECTION

PATENT NO. : 11,207,163 B2  
APPLICATION NO. : 16/303379  
DATED : December 28, 2021  
INVENTOR(S) : Martin Hohlrieder Page 1 of 1

It is certified that error appears in the above-identified patent and that said Letters Patent is hereby corrected as shown below:

On the Title Page

At section Applicant, Item (71), after the words "A.M.I. Agency for Medical Innovations GmbH", delete "Feldkrich" and insert therefor --Feldkirch--.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*